(12) United States Patent
Dudley et al.

(10) Patent No.: US 6,627,887 B1
(45) Date of Patent: Sep. 30, 2003

(54) SYSTEM AND METHOD FOR CONSTRUCTING A PROFILE OF A STRUCTURE IN AN INTEGRATED CIRCUIT

(75) Inventors: Ian Dudley, Santa Clara, CA (US); Jean Yang, Sunnyvale, CA (US); Paula Rao, Santa Clara, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 542 days.

(21) Appl. No.: 09/597,187

(22) Filed: Jun. 20, 2000

(51) Int. Cl.$^7$ .............................................. G01N 23/00
(52) U.S. Cl. ....................... 250/310; 250/306; 250/307; 250/311; 250/397; 250/398; 250/492.1; 250/491.1
(58) Field of Search ..................... 250/306–311, 396 R, 250/492.1–492.3, 397, 398

(56) References Cited

U.S. PATENT DOCUMENTS

| | | | |
|---|---|---|---|
| 4,733,074 A | * 3/1988 | Kato et al. .................. 250/307 |
| 4,767,926 A | * 8/1988 | Murakoshi et al. ......... 250/310 |
| 4,804,840 A | * 2/1989 | Ichihashi .................... 250/310 |
| 5,434,409 A | * 7/1995 | Tsubusaki ................... 250/307 |
| 5,594,245 A | * 1/1997 | Todokoro et al. ........... 250/310 |
| 5,750,990 A | * 5/1998 | Mizuno et al. ............. 250/307 |
| 6,054,710 A | * 4/2000 | Bruggeman ................. 250/307 |
| 6,157,032 A | * 12/2000 | Into ........................... 250/310 |
| 6,326,618 B1 | * 12/2001 | Kane et al. ................. 250/307 |

OTHER PUBLICATIONS

Literature for VeraSEM 3D Metrology SEM manufactured by Applied Materials, Inc., Dec. 1999, pp. 1–2.

* cited by examiner

Primary Examiner—John R. Lee
Assistant Examiner—David A. Vanore
(74) Attorney, Agent, or Firm—Renner, Otto, Boisselle & Sklar, LLP (57) ABSTRACT

A system and method are provided for profiling a structure in an integrated circuit to determine the structural dimensions. The system comprises a processor circuit that includes a processor electrically coupled to a local interface and a memory electrically coupled to the local interface, where the local interface comprises, for example, a data bus and associated control bus. The system further comprises a critical dimension scanning electron microscope having a signal output electrically coupled to the local interface and operating logic stored on the memory and executable by the processor. The operating logic comprises logic to execute a scan of a structure in an integrated circuit using the SEM, logic to store a first derivative waveform generated from the scan in the memory, and logic to generate a profile of the structure from the first derivative waveform.

32 Claims, 6 Drawing Sheets

SYSTEM AND METHOD FOR CONSTRUCTING A PROFILE OF A STRUCTURE IN AN INTEGRATED CIRCUIT

TECHNICAL FIELD

The present invention is generally related to the manufacture of integrated circuits and, more particularly, is related to a system and method for constructing a profile of a structure in an integrated circuit.

BACKGROUND OF THE INVENTION

In the manufacture of integrated circuits, many structures such as circuit elements are created that are microscopic in size. These are generally created using various well known techniques such as photolithography. Photolithography generally involves the creation of a circuit pattern that is photographed and reduced to a negative called the photomask that has a desired final size. Next, light is generally passed through the photomask onto a wafer that comprises a semiconductor material that is coated with photoresistive material. For those locations upon which the light falls, the composition of the photoresistive material is changed. Thereafter, the photoresistive material that has been subjected to light is washed off and, finally, the semiconductor material is subjected to an etching solution that eats away the surface not protected by the photoresistive material. The structures that remain in the semiconductor material make up the resulting circuit pattern on the surface of the wafer.

As a manufacturing method, photolithography has seen great advances in more recent times. Where the first integrated circuits made could only include a relatively small number of circuit elements, currently integrated circuits can be manufactured with millions of circuit elements. This is due, in part, to the fact that advancements in photolithography have resulted in greater resolution and corresponding circuit density. Accompanying the greater density of circuits has been a steady increase in the speeds at which these circuits operate.

Even with advancements with the density and speed of operation of integrated circuits, current manufacturing processes are not without problems. Specifically, from time to time some structures such as conductive pathways may not meet required specifications in terms of size and cross-sectional dimensions among other parameters. Unfortunately, it can be rather difficult and expensive to determine whether the specific size and/or cross-section of a particular structure meets acceptable standards.

SUMMARY OF THE INVENTION

In light of the foregoing, the present invention provides a system and method for profiling a structure in an integrated circuit to determine the structural dimensions. In one embodiment, the system comprises a processor circuit that includes a processor electrically coupled to a local interface and a memory electrically coupled to the local interface, where the local interface comprises, for example, a data bus and an associated control bus. The system further comprises a critical dimension scanning electron microscope (CD-SEM) having a signal output electrically coupled to the local interface and operating logic stored on the memory and executable by the processor. The operating logic comprises logic to logic to execute a scan of a structure in an integrated circuit using the SEM, logic to store a first derivative waveform in the memory, the first derivative waveform being generated from a dimensional waveform that is generated from the scan, and, logic to generate a profile of the structure from the first derivative waveform.

The present invention can also be viewed as providing a method for profiling a structure in an integrated circuit. In this regard, the method can be broadly summarized by the following steps: measuring the structure with a scanning electron microscope (SEM) to generate a first derivative waveform, and, generating a profile of the structure from the first derivative waveform.

Other features and advantages of the present invention will become apparent to one with skill in the art upon examination of the following drawings and detailed description. It is intended that all such additional features and advantages be included herein within the scope of the present invention.

BRIEF DESCRIPTION OF THE SEVERAL VIEWS OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE INVENTION

Figure 1:
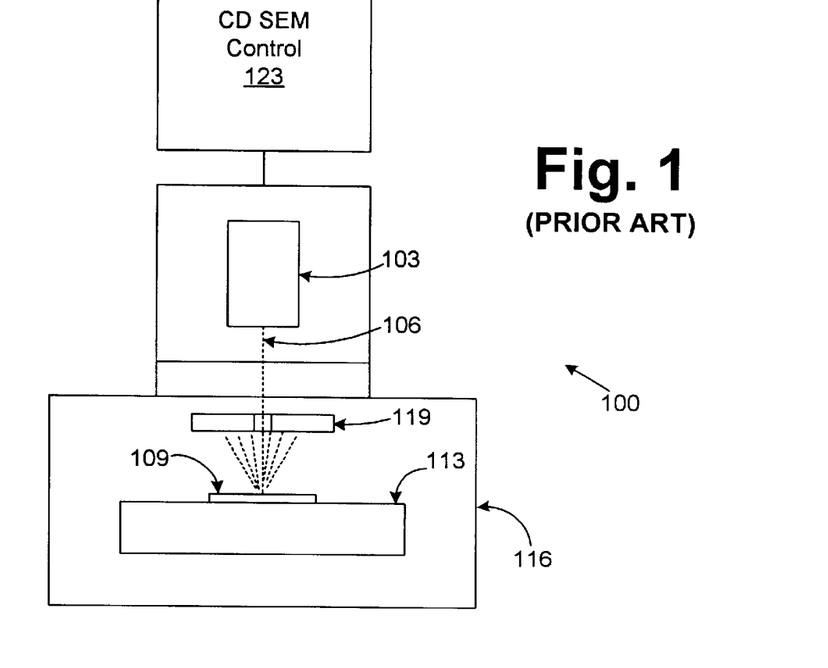
FIG. 1 is block diagram of a critical dimension scanning electron microscope according to the prior art.

Turning to FIG. 1, shown is a critical dimension scanning electron microscope (CD-SEM) 100 according to the prior art. The CD-SEM 100 includes an electron beam source 103 that generates an electron beam 106. The electron beam 106 is directed toward a particular wafer 109 that is to be examined. The wafer 109 is placed on a wafer stage 113 within a vacuum chamber 116. The CD-SEM 100 further includes an electron detector 119 that comprises a number of sensors that detect the presence of electrons that are deflected from the wafer 109 thereby generating a resulting signal. The CD-SEM 100 also includes a CD-SEM control module 123 that generally controls the operation of the CD-SEM 100 as known in the art. The CD-SEM 100 may be, for example, an Applied Materials Model 7830Si CD-SEM manufactured by Applied Materials, Inc. of Santa Clara, Calif. or other similar device.

Figure 2:
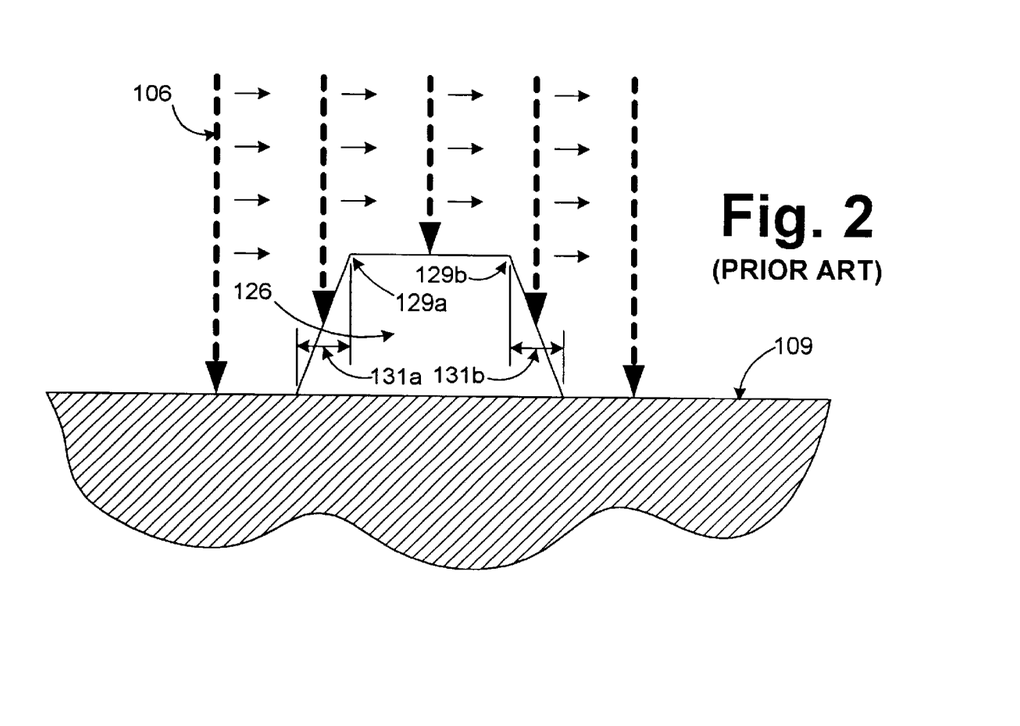
FIG. 2 is a block diagram of a scan of a structure on an integrated circuit using the critical dimension scanning electron microscope of FIG. 1.

Referring next to FIG. 2, shown is a scan of a particular structure 126 on the wafer 109 by the electron beam 106. In particular, the electron beam 106 is scanned over the structure 126 as shown. Many of the electrons that strike the various surfaces of the structure 126 and the wafer 109 are deflected back to the electron detector 119 (FIG. 1) and a resulting waveform is generated therefrom. This waveform is referred to as a dimensional waveform from which information about the structure 126 is obtained as will be discussed. The structure 126 includes left and right edges 129a and 129b as well as left and right structure edge widths 131a and 131b as shown.

Figure 3A:
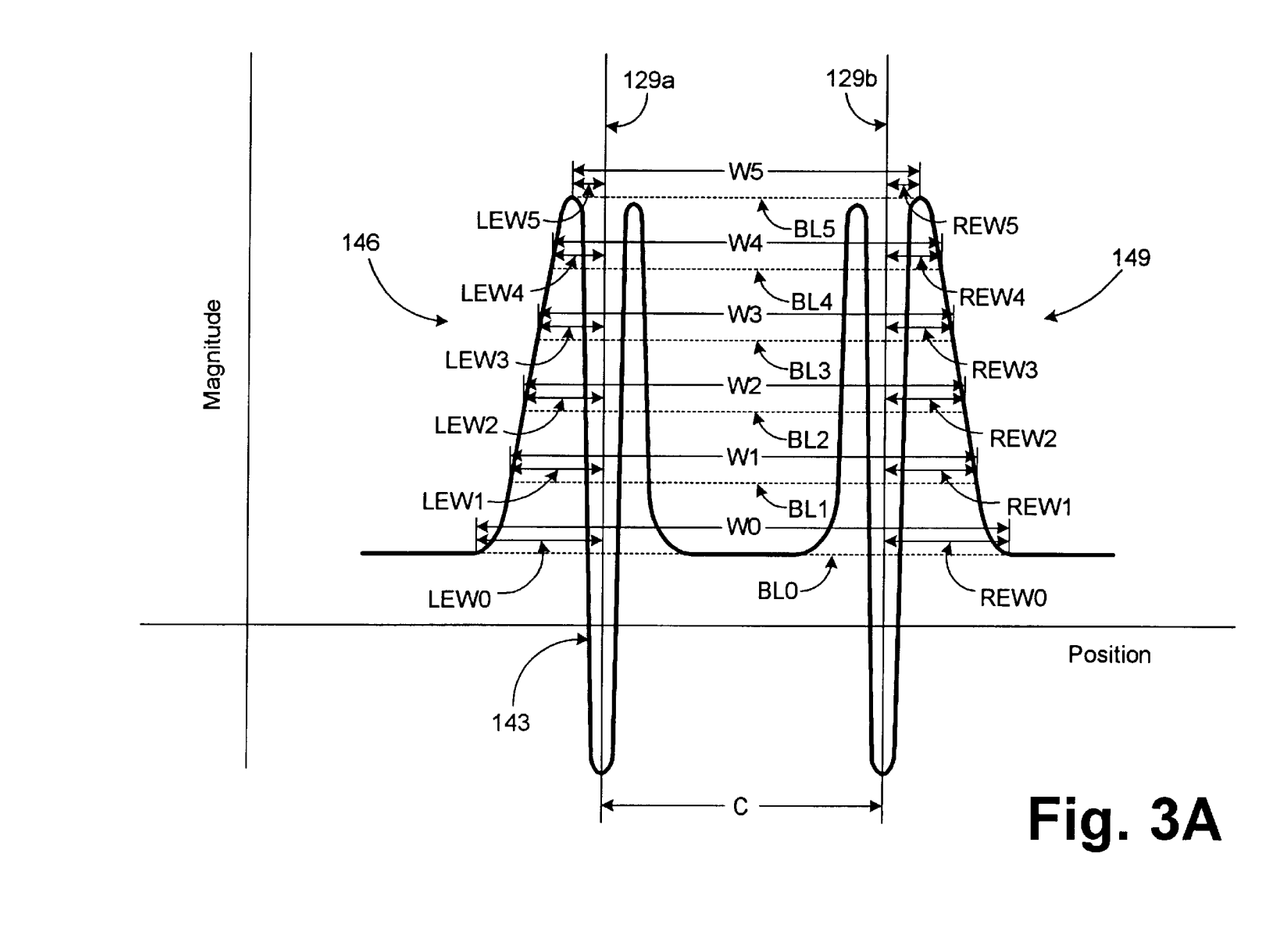
FIG. 3A is a graph of a first derivative waveform generated from the scan of the structure as depicted in FIG. 2.

With reference to FIG. 3A, shown is a graph of the magnitude of a first to derivative waveform 143 with respect to position according to an embodiment of the present invention. The first derivative waveform 143 is the first derivative of the dimensional waveform discussed above that advantageously facilitates the determination of the structure edge widths 131a (FIG. 2) and 131b (FIG. 2) as will be discussed.

The first derivative waveform 143 includes a left peak 146 and a right peak 149. Disposed over the first derivative waveform 143 are a number of baselines BL0–5. The baselines BL0–5 are located at discrete baseline percentage levels defined as specific percentages of the total height of the peaks 146 and 149. The baseline percentage levels are 0%, 20%, 40%, 60%, 80%, and 100% as shown, although any number or combination of percentage levels may be used with the goal of obtaining a representative cross section of the structure 126. Each baseline BL0–5 includes a width W0–5 that extends from the outer edge of the right peak 146 to the outer edge of the left peak 149. Also, the center distance C is indicated relative to the first derivative waveform 143 as being the distance between the first negative peak 151 and the second negative peak 152.

In addition, the left edge widths LEW0–5 are shown as the distance between the outer edge of the left peak 146 and the left boundary 129a of the center distance C at each baseline BL0–5. Likewise, the right edge widths REW0–5 are indicated as the distance between the outer edge of the right peak 149 and the right boundary 129b of the center distance C at each baseline BL0–5.

By establishing the center distance C, the left edge widths LEW0–5, and the right edge widths REW0–5, a general profile of the structure 126 may be recreated.

This may be done, for example, by determining the widths W0–5 of each baseline BL0–5 and then identifying the corresponding left edge widths LEW0–5 and right edge widths REW0–5 using the CD-SEM 100. In particular, a specific baseline percentage level is entered into the CD-SEM 100 and an output is obtained that includes the width W0–5 of the particular baseline BL0–5 and the corresponding left edge width LEW0–5 and right edge width REW0–5.

Note, however, that no parameters should be taken at a baseline percentage level below a predetermined threshold at which the levels of noise generated along with the dimensional waveform diminish the accuracy of the parameters to an unacceptable level. Although a low level of 0% is indicated in FIG. 3A, the lowest percentage level may be, for example, 40% of the height of the peaks 146 and 149 to ensure reliable output values. Likewise, any baseline calculations taken above the .height of the left and right peaks 146 and 149 is also subject to noise and therefore, any measurements above these points should be discarded.

Figure 3B:
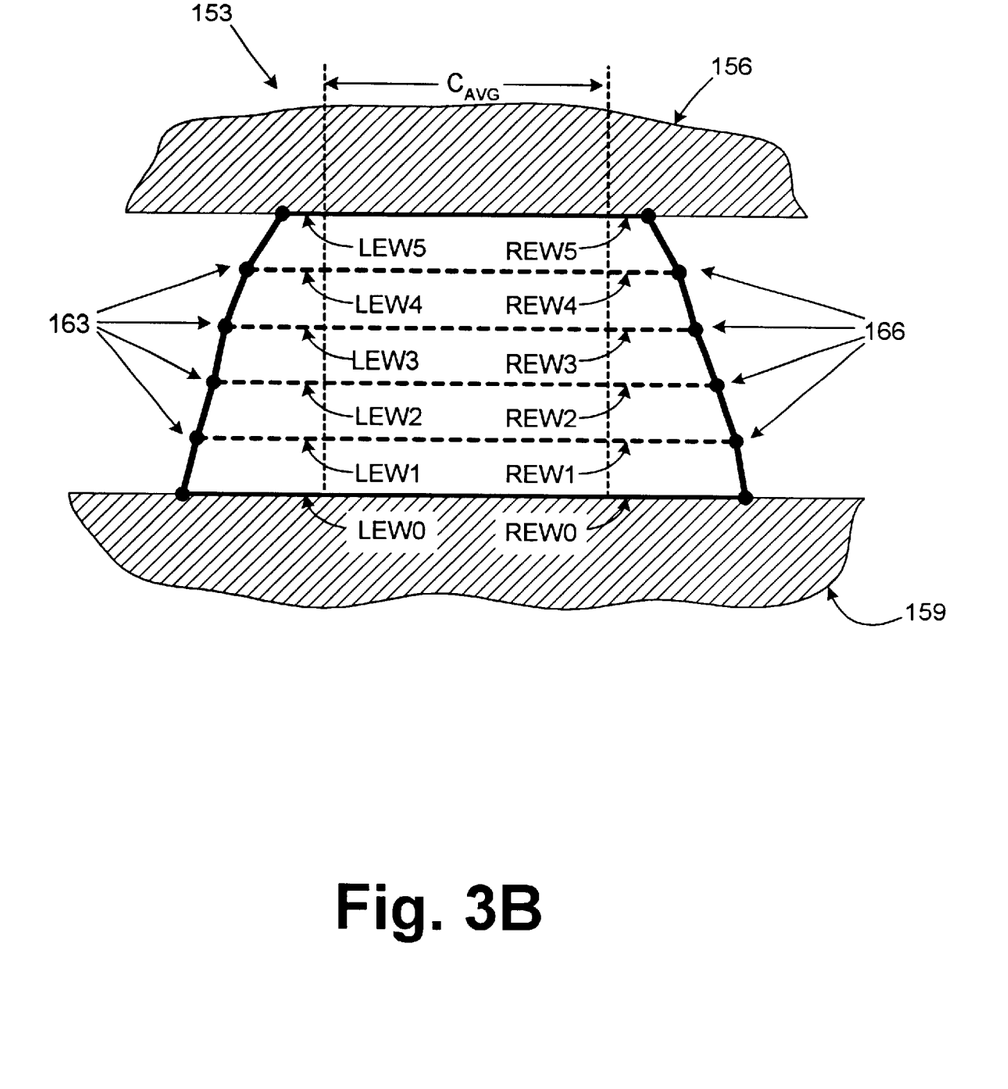
FIG. 3B is a drawing of a profile of the structure of FIG. 2 according to the present invention.

Turning to FIG. 3B, shown is a profile 153 of the structure 126 (FIG. 2) according to an embodiment of the present invention. The profile 153 includes an upper limit region 156 and a lower limit region 159 within which edge widths LEW0–5 and REW0–5 are not obtained due to inaccuracies because of noise and other phenomena. In order to properly plot the profile 153, first baseline parameters including the widths W0–5, left edge widths LEW0–5, and right edge widths REW0–5 are obtained at the predefined baseline percentage levels. For each set of baseline parameters, the center distance C is calculated by subtracting the sum of the left and right edge widths LEW0–5 and REW0–5 from the width W0–5. Unfortunately, this often results in different values for the center distance C along the baselines BL0–5, most likely due to noise, etc. Consequently, to account for the variation in the center distance C at the different baselines BL0–5, an average center distance $C_{AVG}$ is calculated from the center distances and plotted accordingly. Note that another suitable calculation may be made other than averaging to determine a center distance C that is plotted.

Thereafter, the left edge widths LEW0–5 are plotted from the left side of the center distance C along the appropriate baselines BL0–5 (FIG. 3A) to determine the locations of the left points 163 relative to the average center distance $C_{AVG}$. Likewise, the right edge widths REW0–5 are established on the right side of the average center distance $C_{AVG}$ to determine the locations of the right edge points 166. Although the upper and lower limit regions 156 and 159 do not allow plotting of edge points within their bounds due to the concerns of noise as discussed previously, the area of the profile 153 that can be plotted provides enough information to determine whether the profile 153 is acceptable for the purposes for which the structure 126 is intended. The profile 153 may be manually constructed, for example, by plotting the connecting the left edge points 163 and the right edge points 166 and "connecting the dots" as shown.

Figure 4:
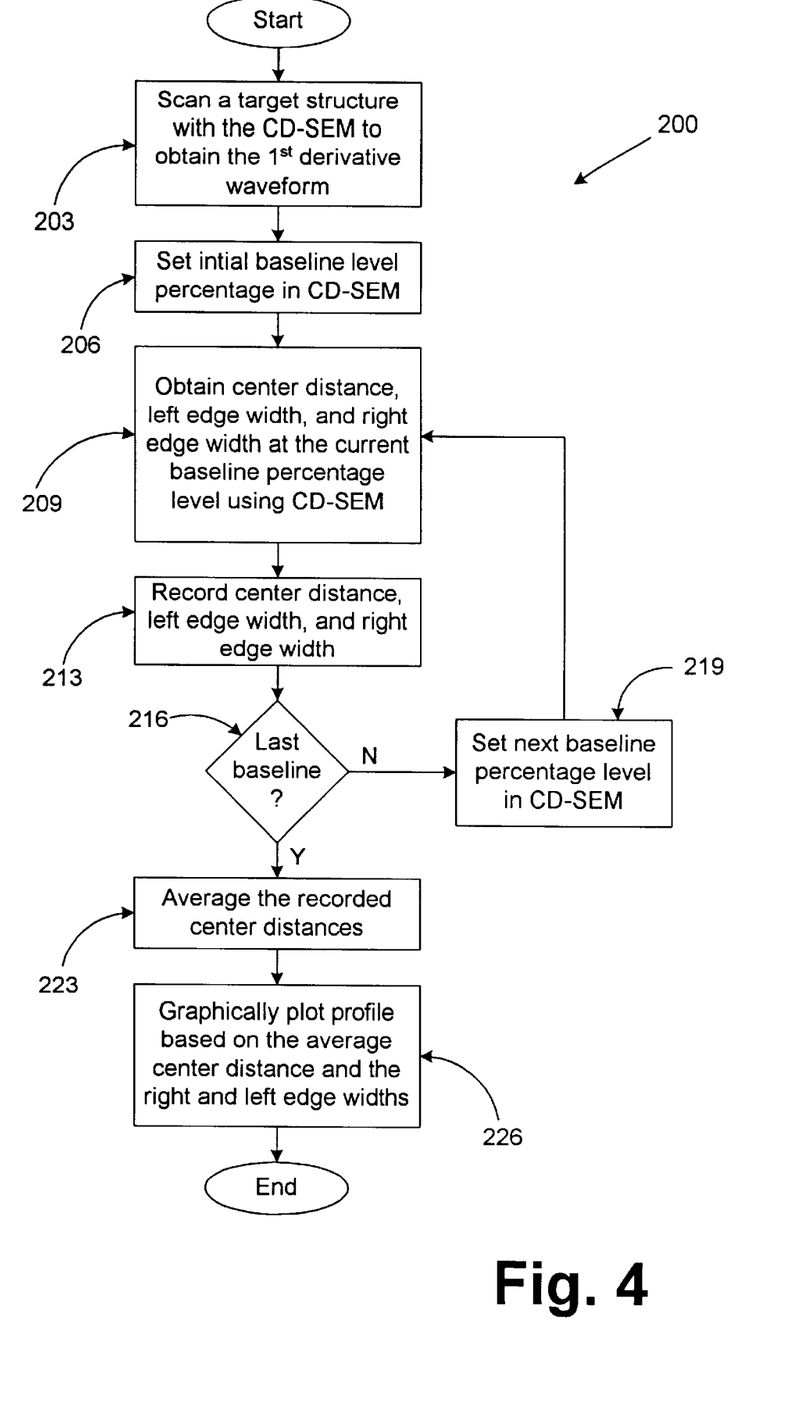
FIG. 4 is a flow chart of a method for generating the profile of FIG. 3B.

With reference to FIG. 4, shown is a flow chart of a profile construction method 200 for manually constructing the profile 153 (FIG. 3B) of a structure 126 (FIG. 2) using the CD-SEM 100. Beginning with step 203, the target structure 126 is scanned with the CD-SEM 100 (FIG. 1) to obtain the dimensional waveform from which the first derivative waveform 143 (FIG. 3A) is generated. Next, in step 206, an initial baseline percentage level is set in the CD-SEM 100 to identify the first baseline BL0 at which the first width W0, right edge width REW0, and left edge width LEW0 are to be obtained.

The method 200 continues with step 209 in which the width Wn, left edge width LEWn, and right edge width REWn are obtained from the CD-SEM 100 along the current baseline BL0 identified by the current baseline percentage level setting. Thereafter, in step 213, the width Wn, left edge width LEWn, and the right edge width REWn from the current baseline BLn are recorded for future reference. Then, in block 216, it is determined whether parameters have been taken from the last baseline BLN, where there are N total baselines BLn. If not, then step 219 is performed in which the next baseline percentage level is set in the CD-SEM 100. Thereafter, method steps 209 through 216 are repeated.

On the other hand, if parameters have been obtained from the last baseline BLN, then method step 223 is performed in which an average value for the center distance $C_{AVG}$ is determined. Alternatively, another acceptable value for the center distance C may be determined to enable plotting of the profile 153. Thereafter, in step 226 the profile 153 is graphically plotted based on the average center distance $C_{AVG}$, the left edge widths LEW0–N, and the right edge widths REW0–N that were previously recorded. Specifically, the baselines BL0–N may be plotted and then the average center distance C plotted thereon. Finally, the left and right edge widths LEW0–N and REW0–N are plotted on each baseline BL0–N extending from the corresponding left and right intersections of the average center distance $C_{AVG}$ and the appropriate baselines. Thereafter, the edge points 163 and 166 (FIG. 3B) are connected to generate the profile 153.

Figure 5:
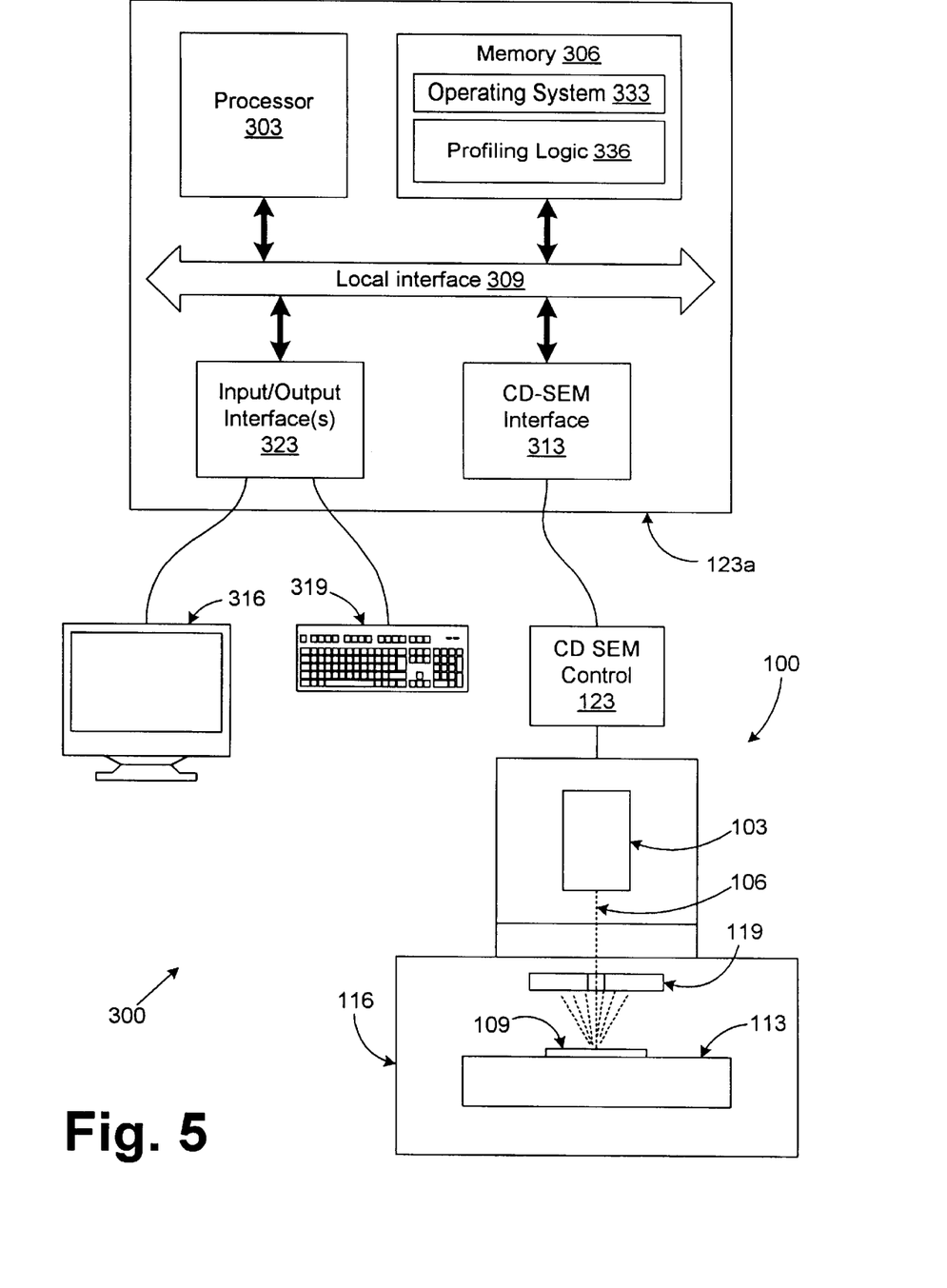
FIG. 5 is a block diagram of a system for generating the profile of FIG. 3B.

Turning to FIG. 5, shown is a profiling system 300 according to an embodiment of the present invention. The profiling system 300 includes the CD-SEM 100 as well as additional control components. In particular, the profiling system 300 includes a processor control system 123*a* that comprises a processor 303, a memory 306, both of which are electrically coupled to a local interface 309. The local interface 309 may comprise, for example, a data bus and an associated control bus. The control system 123*a* also includes a CD-SEM interface 313 that electrically couples the CD-SEM Control 123 to the local interface 309. The CD-SEM interface 313 allows the control system 123*a* to initiate the pertinent functions of the CD-SEM 100 as well as to make waveform information, specifically the first derivative waveform 143 (FIG. 3A), available on the local interface 309.

The control system 123*a* also includes a number of input and output devices such as, a display device 316 and a keyboard 319 that are electrically coupled to the local interface 309 through various input and output interfaces 323. The display device 316 may comprise, for example, a cathode ray tube (CRT), a liquid crystal display screen, a gas plasma-based flat panel display, indicator lights, light emitting diodes, or another type of suitable display device.

The memory 306 includes both volatile and nonvolatile memory components. Volatile components are those that do not retain data values upon loss of power. Conversely, nonvolatile components retain data upon a loss of power. Thus, the memory 306 may comprise any one or a combination of, for example, random access memory (RAM), read-only memory (ROM), hard disk drives, floppy disk drives, compact disk drives, tape drives, and/or other suitable memory components.

Stored on the memory and executable by the processor 303 is an operating system 333 and profiling logic 336. The operating system 333 comprises logic that controls the general operations of the control system 123*a* as known in the art. The profiling logic 336 controls the overall profiling system 300 and also constructs a profile 153 (FIG. 3B) of a scanned structure 126 (FIG. 2) as will be described.

Figure 6:
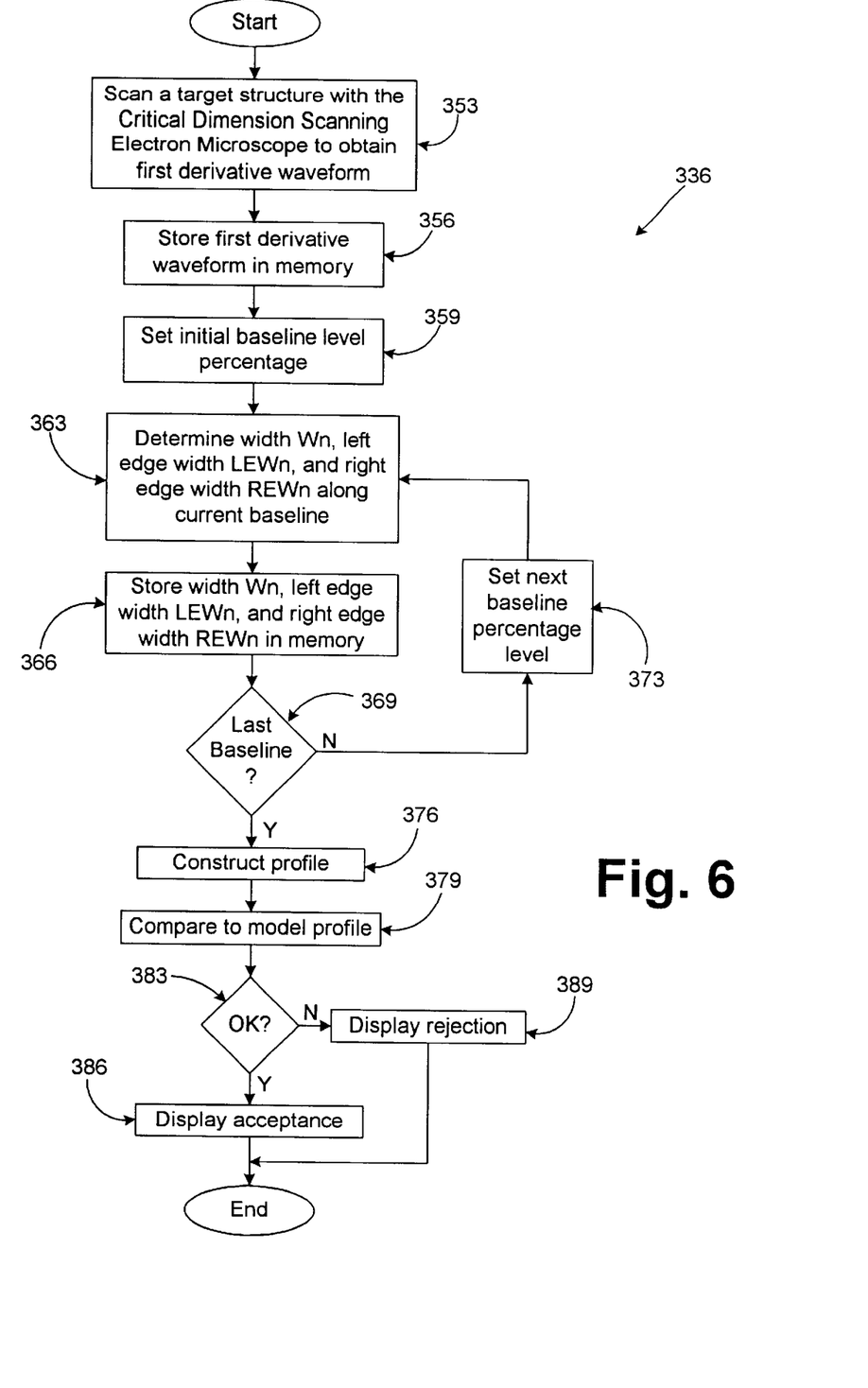
FIG. 6 is a flow chart of logic executed by the system of FIG. 5.

With reference to FIG. 6, shown is a flow chart of the profiling logic 336 according to an embodiment of the invention. The profiling logic 336 is stored on the memory 306 and executable by the processor 303 to obtain a profile 153 (FIG. 3B) of a particular structure 126. In addition, the profiling logic 336 performs a comparison between the profile 153 and a standard or target profile to determine whether the structure 126 meets acceptable standards.

Beginning with block 353, a structure such as the structure 126 (FIG. 1) is scanned with the CD-SEM 100 to obtain the first derivative waveform 143 (FIG. 3A). Thereafter, in block 356, the first derivative waveform 143 is stored in the memory 306. Next, in block 359, an initial baseline level percentage is set to obtain the first width W0, first left edge widths LEW0, and the first right edge width REW0 along the first baseline BW0. The initial and later baseline percentages may be, for example, manually entered into the memory 306 (FIG. 5) via the keyboard 319 for future use by the profiling logic 336.

Thereafter, in block 363, the width Wn, left edge width LEWn, and the right edge width REWn of the current baseline at the current baseline level percentage are determined. Then, in block 366, the current width Wn, left edge width LEWn, and right edge width REWn obtained in block 363 are stored in the memory 306. Next, in block 369, it is determined whether the parameters have been determined along the last baseline at the last identified base level percentage. If not, then the profiling logic 336 moves to block 373 in which the next baseline percentage level is set and thereafter, the profiling logic 336 reverts back to block 363. Otherwise, the profiling logic 336 progresses to block 376 in which the profile 153 (FIG. 3B) is constructed and stored in the memory 306. In particular, the average center distance $C_{AVG}$ is determined and the positions of left edge points 163 and the right edge points 166 are plotted relative to the average center distance $C_{AVG}$ as was discussed. The profile 153 may be represented by a particular graphical presentation that shows the general dimensions of the structure 126 represented thereby.

Then in block 379, the profile 153 is compared to a standard or target profile to determine whether the slopes of the left and right edge widths 131*a* (FIG. 2) and 131*b* (FIG. 2) are within acceptable limits as well as whether the shape of the profile 153 is also acceptable as compared to other preidentified parameters. In block 383, if the profile 153 is acceptable, then the profiling logic 336 moves to block 386 where an acceptance indication is displayed on the display device 316 (FIG. 5). Note that in addition, a graphical plot of the profile 153 may also be generated on the display device 316 if the device features such capability. However, if in block 383, the constructed profile 153 is unacceptable, then the profiling logic 336 moves to block 389 in which a rejection of the structure 126 is indicated on the display device 316 and, correspondingly, the wafer 109 that contains the structure 126 may be rejected. By determining whether or not structures 126 on various wafers 109 (FIG. 5) conform to predetermined standards, a significant advantage is obtained in that quality control of the manufacturing process can be monitored and maintained appropriately.

Although the logic 336 of the present invention is embodied in software as discussed above, as an alternative the logic 336 may also be embodied in hardware or a combination of software and hardware. If embodied in hardware, the logic 336 can be implemented as a circuit that employs any one of or a combination of a number of technologies. These technologies may include, but are not limited to, discrete logic circuits having logic gates for implementing various logic functions upon an application of one or more data signals, application specific integrated circuits having appropriate logic gates, programmable gate arrays (PGA), field programmable gate arrays FPGA, or other components, etc. Such technologies are generally well known by those skilled in the art and, consequently, are not described in detail herein.

The flow chart of FIG. 6 shows the architecture, functionality, and operation of an implementation of the logic 336. If embodied in software, each block may represent a module, segment, or portion of code that comprises one or more executable instructions to implement the specified logical function(s). If embodied in hardware, each block may represent a circuit or a number of interconnected circuits to implement the specified logical function(s). Although the flow chart of FIG. 6 shows a specific order of execution, it is understood that the order of execution may differ from that which is depicted. For example, the order of execution of two or more blocks may be scrambled relative to the order shown. Also, two or more blocks shown in succession in FIG. 6 may be executed concurrently or with partial concurrence. It is understood that all such variations are within the scope of the present invention.

Also, the logic 336 can be embodied in any computer-readable medium for use by or in connection with an instruction execution system such as a computer/processor based system or other system that can fetch or obtain the logic from the computer-readable medium and execute the instructions contained therein. In the context of this document, a "computer-readable medium" can be any medium that can contain, store, or maintain the logic 336 for use by or in connection with the instruction execution system. The computer readable medium can comprise any one of many physical media such as, for example, electronic, magnetic, optical, electromagnetic, infrared, or semiconductor media. More specific examples of a suitable computer-readable medium would include, but are not limited to, a portable magnetic computer diskette such as floppy diskettes or hard drives, a random access memory (RAM), a read-only memory (ROM), an erasable programmable read-only memory, or a portable compact disc read-only memory (CDROM).

Many variations and modifications may be made to the above-described embodiment(s) of the invention without departing substantially from the spirit and principles of the invention. All such modifications and variations are intended to be included herein within the scope of the present invention.

What is claimed is:

1. A system for profiling a structure in an integrated circuit, comprising:
    a processor electrically coupled to a local interface;
    a memory electrically coupled to the local interface;
    a scanning electron microscope (SEM) having a signal output electrically coupled to the local interface; and
    operating logic stored on the memory and executable by the processor, the operating logic comprising:
        logic to execute a scan of a structure in an integrated circuit using the SEM;
        logic to store a first derivative waveform in the memory, the first derivative waveform being the mathematical first derivative of a dimensional waveform that is generated from the scan; and
        logic to generate a profile of the structure from the first derivative waveform.

2. The system of claim 1, wherein the logic to generate a profile of the structure from the first derivative waveform further comprises:
    logic to obtain a number of profile parameters from the first derivative waveform, wherein the profile parameters are obtained along a number of baselines associated with a corresponding number of unique baseline percentage levels;
    logic to store the number of profile parameters associated with each of the baselines in the memory; and
    logic to generate the profile of the structure from the profile parameters.

3. The system of claim 1, wherein the operating logic further comprises logic to display the profile on a display device that is electrically coupled to the local interface.

4. The system of claim 1, wherein the operating logic further comprises logic to compare the profile with a target profile.

5. The system of claim 2, wherein the profile further comprises a number of coordinates along a first and second edge of the structure.

6. The system of claim 2, wherein the profile parameters further comprise a right edge width and a left edge width of the structure.

7. A system for profiling a structure in an integrated circuit, comprising:
    means for executing a scan of a structure in an integrated circuit using a scanning electron microscope (SEM);
    means for storing a first derivative waveform in a memory, the first derivative waveform being the mathematical first derivative of a dimensional waveform that is generated from the scan; and
    means for generating a profile of the structure from the first derivative waveform.

8. The system of claim 7, wherein the means for generating a profile of the structure from the first derivative waveform further comprises:
    means for obtaining a number of profile parameters from the first derivative waveform, wherein the profile parameters are obtained along a number of baselines associated with a corresponding number of unique baseline percentage levels;
    means for storing the number of profile parameters associated with each of the baselines in the memory; and
    means for generating the profile of the structure from the profile parameters.

9. The system of claim 7, further comprising means for displaying the profile.

10. The system of claim 7, further comprising means for comparing the profile with a target profile.

11. The system of claim 8, wherein the means for generating the profile of the structure from the profile parameters further comprises means for plotting a number of coordinates along a first and second edge of the structure.

12. The system of claim 8, wherein the profile parameters further comprise a right edge width and a left edge width of the structure.

13. A method for profiling a structure in an integrated circuit, comprising the steps of:
    scanning the structure with a scanning electron microscope (SEM) to generate a dimensional waveform;
    taking the first derivative of the dimensional waveform to generate a first derivative waveform; and
    generating a profile of the structure using the first derivative waveform.

14. The method of claim 13, wherein the step of generating a profile of the structure from the first derivative waveform further comprises the steps of:
    generating a set of profile parameters from the first derivative waveform along each of a plurality of baselines, each baseline corresponding to a unique baseline percentage level; and
    generating the profile from the profile parameters.

15. The method of claim 14, further comprising plotting a number of coordinates from the profile parameters to represent a first and second edge of the structure.

16. The method of claim 13, further comprising the step of comparing the profile with a target profile.

17. The method of claim 14, further comprising ignoring profile parameters associated with a baseline percentage level below a predetermined threshold associated with a noise tolerance when generating the profile of the structure.

18. The method of claim 14, further comprising ignoring profile parameters associated with a baseline percentage level above a predetermined threshold associated with a noise tolerance when generating the profile of the structure.

19. The method of claim 14, wherein the structure has a first edge and a second edge and the first derivative waveform for the structure has a first peak corresponding to the first edge and a second peak corresponding to the second edge.

20. The method of claim 19, wherein the set of profile parameters include a width measured from an outer edge of the first peak to an outer edge of the second peak.

21. The method of claim 19, wherein the first derivative waveform includes a first negative peak associated with the first edge and a second negative peak associated with the second edge.

22. The method of claim 21, wherein the set of profile parameters include a first edge width calculated as a distance from an outer edge of the first peak to a first boundary corresponding to a bottom of the first negative peak and a second edge width calculated as a distance from an outer edge of the second peak to a second boundary corresponding to a bottom of the second negative peak.

23. The method of claim 22, wherein the set of profile parameters include a width measured from the outer edge of the first peak to the outer edge of the second peak.

24. The method of claim 23, further comprising calculating a center distance for each baseline by subtracting the corresponding first edge and second edge widths from the width.

25. The method of claim 24, further comprising averaging each of center distances to generate a center distance value.

26. The method of claim 25, further comprising generating a set of first edge points by plotting the first edge widths relative to a first end of a plotted representation of the center distance value and a set of second edge points by plotting the second edge widths relative to a second end of the representation of the center distance value.

27. A method for profiling a structure in an integrated circuit, comprising the steps of:

executing a scan of a structure in an integrated circuit using a scanning electron microscope (SEM);

generating and storing a first derivative waveform in a memory of a computer system, the first derivative waveform being the mathematical first derivative of a dimensional waveform that is generated from the scan; and generating a profile of the structure in the memory from the first derivative waveform using the computer system.

28. The method of claim 27, wherein the step of generating a profile of the structure in the memory from the first derivative waveform using the computer system further comprises the steps of:

generating a number of profile parameters from the first derivative waveform, wherein the profile parameters are obtained along a number of baselines associated with a corresponding number of baseline percentage levels;

storing the profile parameters in the memory; and generating the profile of the structure in the memory from the profile parameters.

29. The method of claim 27, further comprising the step of displaying the profile on a display device.

30. The method of claim 27, further comprising the step of comparing the profile with a target profile that is stored in the memory.

31. The method of claim 28, wherein the step of generating the profile of the structure in the memory from the profile parameters further comprises the step of plotting a number of coordinates relative to each other along a first edge and a second edge of the structure.

32. The method of claim 28, wherein the step of storing the profile parameters in the memory further comprises the step of storing at least one right edge width and at least one left edge width of the structure in the memory.

* * * * *